United States Patent
Garito et al.

(10) Patent No.: US 7,070,604 B1
(45) Date of Patent: Jul. 4, 2006

(54) RF ELECTROSURGICALLY-ACTIVATED CUTTER

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 534 days.

(21) Appl. No.: 10/265,339

(22) Filed: Oct. 7, 2002

(51) Int. Cl.
*A61B 17/32* (2006.01)
(52) U.S. Cl. ......................... 606/177; 600/10
(58) Field of Classification Search .................. 606/49, 606/45, 166, 171, 32, 33, 37, 39, 42, 50, 606/170; 604/22; 600/10, 11, 564
See application file for complete search history.

(56) References Cited

U.S. PATENT DOCUMENTS

| | | | |
|---|---|---|---|
| 4,108,182 A * | 8/1978 | Hartman et al. | 606/171 |
| 4,246,902 A * | 1/1981 | Martinez | 604/22 |
| 4,314,560 A * | 2/1982 | Helfgott et al. | 606/171 |
| 5,662,680 A * | 9/1997 | Desai | 606/210 |
| 6,565,561 B1 * | 5/2003 | Goble et al. | 606/41 |
| 6,749,608 B1 * | 6/2004 | Garito et al. | 606/45 |

* cited by examiner

*Primary Examiner*—Gary Jackson
*Assistant Examiner*—Victor Nguyen

(57) ABSTRACT

A novel cutter instrument uses radiofrequency (RF) electrosurgery and RF energy to achieve the desired cutting action with minimum of mechanical force, thereby reducing the risk of tissue damage due to excessive mechanical cutting action. Preferably, a cutter head of the instrument comprises an outer tube of electrically-insulating material with an aperture into which is telescoped an inner electrically-conductive tube. When the working or leading end of the latter is reciprocated across the aperture in the outer tube while RF electrosurgical currents are applied to the inner tube, the cutting action of tissue entering the aperture takes place primarily via the RF electrosurgical currents.

5 Claims, 2 Drawing Sheets

RF ELECTROSURGICALLY-ACTIVATED CUTTER

This invention relates to an electrosurgical cutter for carrying out various surgical procedures. In particular, it relates to an electrosurgical cutter instrument of the reciprocating type, and cutter heads for use with such electrosurgical cutters.

BACKGROUND OF THE INVENTION

U.S. Pat. No. 4,108,182, whose contents are hereby specifically incorporated by reference, describes a suction reciprocating cutter head especially useful for removing vitreous material under suction and for other surgical uses. The technique there described applies mechanical forces for shredding and cutting the vitreous into pieces while sucking the cut vitreous to disposal means. Another feature is the use of a protective sheath over the instrument part that provides the reciprocating action coupled with making the cutter head removable, with the result that the latter can be made disposable after use without the need to sterilize the protected instrument part that provides the reciprocating action.

A disadvantage of such an instrument is that, however small the applied mechanical force, there can always be a pulling or pressing force on the vitreous than can cause tearing damage on the vitreous.

SUMMARY OF THE INVENTION

An object of the invention is a cutting instrument that reduces the risk of tearing, spooling, or wind-up damage to the vitreous, as well as to other tissue in other surgical procedures.

Briefly stated, the novel cutter instrument in accordance with a feature of the invention uses radiofrequency (RF) electrosurgery and RF energy to achieve the desired cutting action with minimum mechanical force, thereby reducing the risk of tissue damage due to excessive mechanical cutting action.

In a preferred embodiment, the cutter head comprises an outer tube of electrically-insulating material with an aperture into which is telescoped an inner electrically-conductive tube. When the working or leading end of the latter is reciprocated across the aperture in the outer tube while RF electrosurgical currents are applied to the inner tube, the cutting action of tissue entering the aperture takes place primarily via the RF electrosurgical currents, and the inner tube functions mainly to uncover the aperture to allow tissue to enter and subsequently to cover the aperture to allow the suction to suction away the separated material. Thus, the leading edge of the inner tube, that in the prior art device must be sharpened to function properly, need not be given a particularly sharp edge in the instrument of the invention as it plays a much smaller role than in the prior art device. To provide RF electrosurgical currents at the inner electrically-conductive tube, an electrically-conductive connection is preferably made to a region of the inner tube remote from its leading edge or to an electrically-conductive part that is mechanically and electrically connected to the inner tube. The electrically-conductive connection is terminated by an external connector that can be connected to standard electrosurgical apparatus at a unipolar outlet.

Preferably, the electrosurgical cutter instrument of the invention works best with relatively high-frequency RF electrosurgical currents in excess of 1.5 MHz, preferably in the range of 1.5–4 MHz, as we believe that using electrosurgical currents in the MHz range causes relatively low tissue temperatures avoiding possible damage to adjacent tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Figure 1:
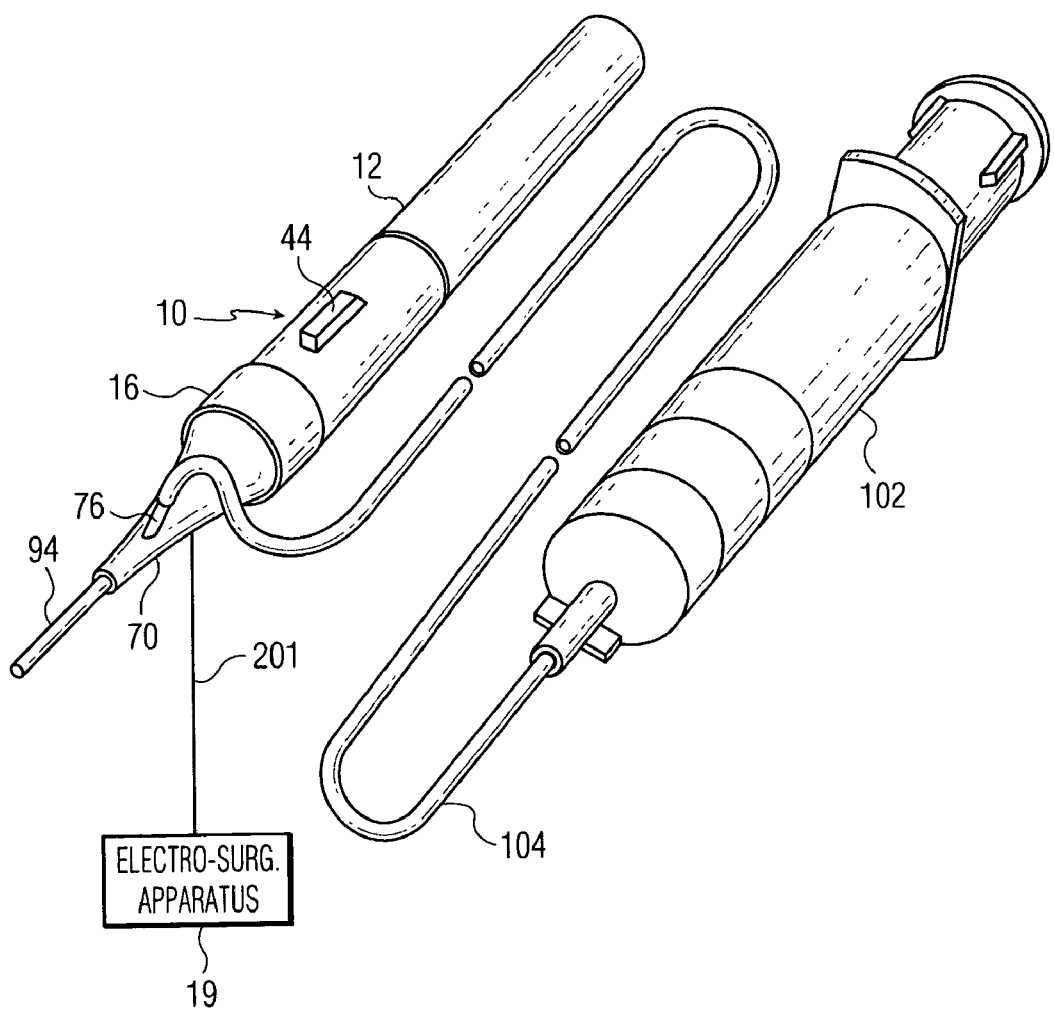
FIG. 1 is a perspective view of one form of electrosurgical cutter instrument of the reciprocating type in accordance with the invention shown connected to suitable electrosurgical apparatus.

The reader is directed to the referenced prior patent which will assist in understanding the improvements offered by the present application. For the convenience of the reader, the same instrument assembly as described in the patent is used to illustrate the invention with the improvements of the present invention incorporated therein. The same reference numerals as used in the drawings of the references patent are also used for the convenience of the reader. The reader is directed to that patent for any further details of the overall assembly construction which are omitted here as unnecessary to a complete understanding of the present invention. More particularly, those skilled in the art will recognize that the invention is not limited to the specific construction of the reciprocating mechanism described in the patent, and other well-known reciprocating mechanisms in similar type instruments are deemed within the scope of the present invention. Moreover, the invention is not limited to cutter constructions in which the cutter head is removable and disposable.

Conventional electrosurgical apparatus can be used with instruments of the invention, but it is preferred to use low-power electrosurgical apparatus. Such apparatus is available from Ellman International of Hewlett, N.Y. as Model IEC50. The latter has the advantage that it generates RF electrosurgical currents in the MHz range, specifically, about 1.5–4 MHz, which we prefer for their less damaging effect on neighboring tissue.

In the preferred embodiment of a reciprocating cutter instrument according to the invention illustrated in FIG. 1, the instrument 10 comprises a drive housing 12 containing on its interior a power source and a conventional motor section. A switch 44 turns the motor on and off. The disposable, removable cutter head 16 when mounted engages a bayonet type connector to maintain the units assembled with the motor shaft engaging and rotating a cam 80 having a cam surface 82 in the cutter head 16.

The RF cutting device 10 of the present invention contains all the parts such as battery, motor, switch, spring coil 86, as described in the patent, but certain critical changes are necessary to implement the invention. These changes include the following.

The housing of the drive section 12, which is generally cylindrical, is made of an electrically-insulating material, such as a suitable plastic. Also, the body 70 of the cutter head 16 also is made of an electrically-insulating material, such as a suitable plastic. In addition, the cam 80 is similarly made of an electrically-insulating material, such as a suitably hard plastic provided with a smooth inclined cam face 82 which contacts an electrically-conductive metal cam follower assembly 84 held against the cam face by an electrically-conductive coil spring 86. Other changes are also necessary which will be explained below.

In this embodiment, the cam follower assembly 84 comprises a periphery which is hexagonal in shape slightly smaller than the hexagonal bore 73 of the body which permits axial movement of the cam follower assembly 84 but which prevents rotation. In this manner, well known in the art, rotary movement of the cam 80 is converted to reciprocating movement of the cam follower 84. Bearing against the reverse side of follower 84 is the metal spring 86 which is seated against an electrically-conductive retaining ring 92, for example, of metal, mounted in the bore 93 of the body 70. The electrically-conductive retaining ring 92 has a wire 201 mechanically bound and soldered to the ring 92 on the side of the bore 93 and is thus electrically connected to the wire 201. The wire 201, which is insulated wire, extends through a tubular extension 202 to an external small electrical jack 203, to which it may be connected by, for example, a quick banana connector (not shown) to the unipolar outlet of an electrosurgical generator 19 via the usual cable.

The generated RF energy from the electrosurgical generator 19 will go through the cable to the wire 201, the conductive retaining ring 92, the conductive coil spring 86, and then the cam follower 84 which has a hollow cutting inner electrically-conductive tube blade 95, for example, of metal, mounted in the bore 93 in the stem of the cam follower and reciprocates therewith. The inner electrically-conductive tube 95 is positioned within an outer stationary electrically-insulating, for example, of hard plastic, outer tube 94 fixed to the end of the nose body in a plastic cap member 97. The inner metal cutting tube blade 95 and the outer plastic tube 94 may be of any configuration as long as they are matched for a close telescoping fit in the area where tissue cutting or separation takes place. As in the instrument described in the patent, a tubular extension 76 provides access to the inner bore 71. The extension 76 in turn is coupled to a conduit 104 which terminates in a suction-generating device 102. The inner tube 95 is also provided with an aperture 151 which provides access to the hollow inner tube interior. When suction is activated, the bore 71 is emptied as well as the hollow inner tube 95 when the tube is in its retracted position and the tube aperture 151 exposed. At the distal end of the structure, to the left in FIG. 2, the outer tube end is closed off 99 except for an aperture 98 which provides access for tissue into the distal end of the outer tube 94. In the patent arrangement, when the inner tube 95 is reciprocated to its forward extended position, the open cutter end 101 of the inner tube 95 traverses the aperture 98 thereby slicing off or separating, and receiving in the hollow inner tube 95, any tissue drawn by the suction through the aperture 98 into the interior of the hollow outer tube 94. The suction then suctions away the tissue or any fluids present via the aperture 151 and the tubular extension 76 to the collecting means of the suction generator 102.

In the inventive instrument, however, the tissue excision takes place mainly due to the RF energy supplied by the electrosurgical apparatus 19 which is present at the electrically-conductive end 101 of the inner tube 95, substantially free of the mechanical pressing force of the prior art device. The return path for the RF energy is the usual large indifferent plate placed in contact with the patient. The aperture 98 in the outer plastic tube 94 may be of any preferred shape or size in the side wall near the end of the outer plastic tube 94 to permit entry of the tissue, especially, vitreous material, when suction is applied.

The relative lengths of the inner 95 and outer 94 tubes are such that the open end 101 of the inner tube 95, which may or may not be sharpened, passes across the aperture 98 with each down stroke of the cam 80. Each upstroke of the cam 80 uncovers the aperture 98 to permit entry of fresh vitreous or other tissue material. The upstroke is accomplished by the action of the conductive coil spring 86 which is sealed on the retaining ring 92 pushing against the force of the cam follower 84 and driving it towards the cam face 82. The down stroke action of the blade 95 with RF energy at its working end 101 disintegrates the vitreous material between the tube end 101 of the inner tube 95 and the edge of the aperture 98. It is not necessary to have a sharp cutting surface for the aperture, since the cutting is mainly by the RF energy, and very little, if any, pressing force is required. The cam follower assembly is mounted in the retainer ring 92 which abuts a circular seal 100 to prevent entry of foreign material from cavity 71 into the bore 52 of the cutter head. The reciprocating cutter tube blade 95 is also provided with the aperture 151 which allows the cut vitreous or tissue or fluids to be drawn upward through the inside diameter of the inner cutting tube 95 and out through the opening 151 into the suction chamber 71 and then into the syringe 102.

The external fixed thin wall tube 94 projects from the end of the body 70 with the distal end 99 being formed into a smoothly blended non-conductive enclosure to prevent any unintended scattering of RF energy.

The conductive retaining ring 92 and seal 100 are mounted around the cam follower 84 to keep fluids from entering into the cavity housing the coupling means, thus preventing any leakage of vitreous material, fluid, blood or other materials past the shaft. The seal also prevents air from being drawn into the syringe via motor shaft leakage. The cam follower shaft 105 and ring 92 and seal 100 effectively seal off bore 71 to form the fluid receiving chamber 71. It is important to confine the RF energy in the controlled area adjacent the distal end 101 of the electrically-conductive inner tube 95.

It will be appreciated that, in the preferred embodiment, the outer parts of the structure are electrically insulating to prevent accidental electrical shock to the surgeon or patient and prevent inadvertent tissue damage upon contact. The electrically-conductive parts which carry the RF electrosurgical currents are all buried within the structure. In order to transmit the RF energy from the wire 201 to the inner tube 95, the wire is electrically connected to the conductive retaining ring 92 which in operation is axially fixed. The electrical path is from the retaining ring 92 to the electrically-conductive spring 86 to the electrically-conductive cam follower 84 and thereby to the electrically-conductive inner tube 95 which is mounted to the cam follower 84 via the shaft 105. Of those parts, only the retaining ring 92 is immovable and thus the preferred wire connecting member. Extending the wire 201 to connect to the reciprocating cam follower shaft 105 or directly to the inner tube 95 is also possible, but has the possible disadvantages of constant flexing of the wire end that may reduce its lifetime and exposure of the wire end to the withdrawn body fluids. However, this is less of a problem with a disposable cutter head which undergoes only one use before being thrown out. By also making the cam 80 of electrically-insulating material prevents the RF energy from flowing back to the power source, which may include control circuitry, that may be damaged by the RF energy.

Figure 2:
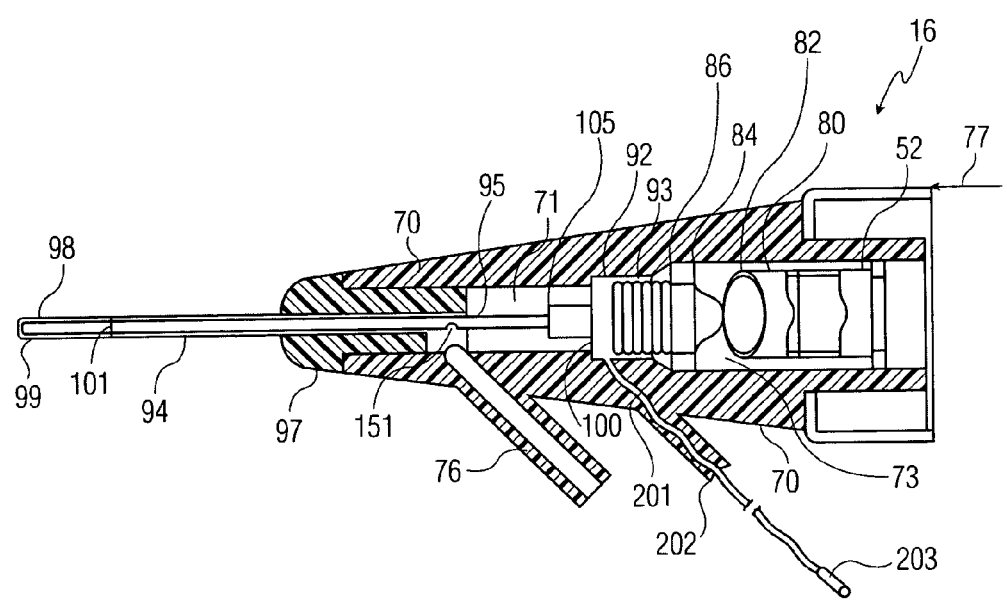
FIG. 2 is a cross-sectional view along the longitudinal axis of the removable cutter head of the embodiment of FIG. 1.

The structure 77 at the right end of FIG. 2 is for mounting of the cutter head 16 to the power assembly 12.

The surgical procedure is as follows. Only the steps relative to the invention are recited in broad terms. The cutter 10 is connected in the usual way to the electrosurgical apparatus 19. The surgeon inserts the working end 99 into the tissue to be excised and removed. The surgeon then activates the electrosurgical apparatus 19 choosing operating parameters such that relatively low power, low voltage settings of the apparatus are chosen. For the IEC50 instrument, which generates an output power of about 50 watts, a typical power setting of about 3–8 can be used. These values can be determined beforehand using test tissue, typically animal, and measuring the temperature due to resistive heating in the tissue surrounding the tip of the needle after a reasonable ON time of the instrument, say about 2–10 sec. The goal should be a low tissue temperature of about 50EC. The ON switch of the cutter is then depressed. The tissue inside the aperture 98 and subject to the RF energy from the reciprocating inner tube end 101 disintegrates and is suctioned out by the applied suction. The procedure is otherwise the same as that used with the electromechanical reciprocating cutter. No heating occurs around the electrically-insulating sections, because they are adequately electrically-insulated and no electrosurgical currents flow into the tissue from those sections.

The device described has particular utility for treating viscera disorders.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A cutter head for cutting patient tissue during reciprocation by electrosurgery, comprising:
   a) an outer housing of electrically-insulating material including an axially-projecting electrically-insulating outer tube having a distal end surface formed by a closed end, an aperture located in a side wall of the outer tube adjacent to the distal end of the outer tube for receiving tissue to be cut,
   b) an inner electrically-conductive tube telescoped within the outer tube and having at its distal end an open-ended working end of sufficient length such that when reciprocated between an extended and a retracted position the working end alternately covers and uncovers the outer tube aperture,
   c) means for providing an electrical connection capable of supplying RF electrosurgical currents to the inner tube,
   d) means for reciprocating the inner tube within the outer tube such that, when the inner tube's working end is reciprocated across the aperture in the outer tube while RF electrosurgical currents are applied to the inner tube via the electrical connection, any tissue entering the outer tube aperture is excised primarily via the RF electrosurgical currents.

2. A cutter head as claimed in claim 1, further comprising:
   e) means for providing suction to the interior of the inner tube to remove the excised tissue,
   f) the inner tube comprising a side aperture normally open to the suction means when the inner tube is in its retracted position but is closed to the suction means when the inner tube moves forward to its extended postion.

3. A cutter head as claimed in claim 2, further comprising:
   g) a suction chamber surrounding a portion of the inner tube including the inner tube aperture,
   wherein the means for providing suction comprises means coupled to the suction chamber and accessible externally of the cutter head for connection to a suction source.

4. A cutter head as claimed in claim 1, wherein the means for reciprocating the inner tube comprises a spring-biased cam follower, and an electrically-conductive retaining ring fixed against axial movement and coupled to the spring, the electrical connection being made to the retaining ring.

5. A cutter head as claimed in claim 4, wherein the retaining ring, the spring, and the cam follower are constituted of electrically-conductive material, and the inner tube is mounted to the cam follower.

* * * * *